United States Patent
Al-Huwaider et al.

(10) Patent No.: US 11,802,827 B2
(45) Date of Patent: Oct. 31, 2023

(54) SINGLE STAGE MICP MEASUREMENT METHOD AND APPARATUS

(71) Applicant: Saudi Arabian Oil Company, Dhahran (SA)

(72) Inventors: Mustafa A. Al-Huwaider, Dhahran (SA); Shouxiang Mark Ma, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 29 days.

(21) Appl. No.: 17/539,505

(22) Filed: Dec. 1, 2021

(65) Prior Publication Data
US 2023/0168172 A1 Jun. 1, 2023

(51) Int. Cl.
*G01N 15/08* (2006.01)
*G01N 33/24* (2006.01)

(52) U.S. Cl.
CPC ..... *G01N 15/0826* (2013.01); *G01N 15/0886* (2013.01); *G01N 33/24* (2013.01); *G01N 2015/0813* (2013.01)

(58) Field of Classification Search
CPC .... G01N 15/00; G01N 15/08; G01N 15/0826; G01N 15/0886; G01N 33/24; G01N 2015/0813
See application file for complete search history.

(56) References Cited

U.S. PATENT DOCUMENTS

| 2,372,875 | A |   | 4/1945 | Roy |
| 2,604,779 | A | * | 7/1952 | Purcell ............... G01N 15/0886 |
|   |   |   |   | 324/439 |
| 2,852,230 | A |   | 9/1958 | Garrison |

(Continued)

FOREIGN PATENT DOCUMENTS

| CN | 102619484 | 8/2012 |
| EP | 0514657 | 4/1992 |

(Continued)

OTHER PUBLICATIONS

U.S. Appl. No. 16/863,740, filed Apr. 30, 2020, Al-Huwaider.

(Continued)

*Primary Examiner* — Nguyen Q. Ha
(74) *Attorney, Agent, or Firm* — Fish & Richardson P.C.

(57) ABSTRACT

A single stage high pressure mercury injection capillary pressure measurement apparatus includes a sample sub-assembly, a transducer sub-assembly, a hydraulic intensifier, and a gas cylinder. The sample sub-assembly includes a casing having walls defining an interior volume, a penetrometer arranged in the casing, the penetrometer having walls defining a sample volume, an annular space defined between the walls of the casing and the walls of the penetrometer, and a common chamber fluidly connected to the annular space by a fluid line and to the sample volume of the penetrometer by a tubing. The transducer sub-assembly is fluidly connected to the sample sub-assembly via the common chamber and includes a plurality of high-pressure transducers a plurality of low-pressure transducers. The hydraulic intensifier is fluidly connected to the common chamber and is configured to apply a high pressure to the annular space.

27 Claims, 3 Drawing Sheets

(56) References Cited

U.S. PATENT DOCUMENTS

| | | | |
|---|---|---|---|
| 3,150,727 A | 9/1964 | Garrison | |
| 3,353,612 A | 11/1967 | Bannister | |
| 3,371,520 A | 3/1968 | Slone et al. | |
| 3,807,227 A | 4/1974 | Smith, Jr. | |
| 3,882,714 A | 5/1975 | Libal et al. | |
| 3,903,974 A | 9/1975 | Cullen | |
| 3,981,187 A | 9/1976 | Howell | |
| 4,170,129 A | 10/1979 | Lowell | |
| 4,203,317 A | 5/1980 | Gupta | |
| 4,211,106 A * | 7/1980 | Swanson | G01N 15/0886 73/38 |
| 4,754,839 A | 7/1988 | Rathman | |
| 4,899,112 A | 2/1990 | Clark et al. | |
| 4,929,113 A | 5/1990 | Sheau | |
| 5,497,321 A | 3/1996 | Ramakrishnan et al. | |
| 5,531,112 A | 7/1996 | Young et al. | |
| 5,667,025 A | 9/1997 | Haessly | |
| 5,746,279 A | 5/1998 | Havlinek | |
| 6,028,307 A | 2/2000 | Young et al. | |
| 6,061,634 A | 5/2000 | Belani et al. | |
| 6,188,222 B1 | 2/2001 | Seydoux et al. | |
| 6,298,711 B1 | 10/2001 | Vollkovich et al. | |
| 6,301,959 B1 | 10/2001 | Hrametz et al. | |
| 6,655,462 B1 | 12/2003 | Carmichael et al. | |
| 6,745,835 B2 | 6/2004 | Fields | |
| 7,086,484 B2 | 8/2006 | Smith, Jr. | |
| 7,607,478 B2 | 10/2009 | Martinez et al. | |
| 7,644,610 B2 | 1/2010 | Meister | |
| 7,703,317 B2 | 4/2010 | Goodwin et al. | |
| 7,753,125 B1 | 7/2010 | Penisson | |
| 7,789,170 B2 | 9/2010 | Church | |
| 8,109,140 B2 | 2/2012 | Tustin et al. | |
| 8,265,874 B2 | 9/2012 | Ma et al. | |
| 8,408,307 B2 | 4/2013 | Telfer | |
| 8,496,054 B2 | 7/2013 | Zazovsky et al. | |
| 8,550,184 B2 | 10/2013 | Buchanan et al. | |
| 8,593,140 B2 | 11/2013 | Saldungaray et al. | |
| 8,904,857 B2 | 12/2014 | Tustin et al. | |
| 8,955,584 B2 | 2/2015 | Telfer | |
| 8,978,481 B2 | 3/2015 | Powell et al. | |
| 9,109,417 B2 | 8/2015 | Leiper et al. | |
| 9,303,509 B2 | 4/2016 | Milkovisch et al. | |
| 9,383,476 B2 | 7/2016 | Trehan et al. | |
| 9,442,211 B2 | 9/2016 | Seydoux et al. | |
| 9,752,433 B2 | 9/2017 | Proett et al. | |
| 10,208,582 B2 | 2/2019 | Ma et al. | |
| 10,247,849 B2 | 4/2019 | Pfutzner et al. | |
| 10,316,648 B2 | 6/2019 | Swett | |
| 10,371,619 B2 * | 8/2019 | Marche | G01N 15/0886 |
| 10,526,871 B2 | 1/2020 | Tzallas et al. | |
| 10,545,129 B2 | 1/2020 | Nguyen et al. | |
| 10,626,721 B2 | 4/2020 | Gisolf et al. | |
| 11,015,447 B2 | 5/2021 | Zainalabedin et al. | |
| 2002/0005286 A1 | 1/2002 | Mazorow et al. | |
| 2006/0000606 A1 | 1/2006 | Fields et al. | |
| 2006/0081398 A1 | 4/2006 | Arian | |
| 2007/0261855 A1 | 11/2007 | Brunet et al. | |
| 2008/0066536 A1 | 3/2008 | Goodwin et al. | |
| 2008/0185142 A1 | 8/2008 | Pelletier | |
| 2008/0210420 A1 | 9/2008 | Ramakrishnan et al. | |
| 2009/0008079 A1 | 1/2009 | Zazovsky et al. | |
| 2009/0159278 A1 | 6/2009 | Corre et al. | |
| 2010/0126717 A1 | 5/2010 | Kuchuk et al. | |
| 2011/0272150 A1 | 11/2011 | Ives et al. | |
| 2012/0312530 A1 | 12/2012 | Pope et al. | |
| 2013/0020128 A1 | 1/2013 | Calleri | |
| 2013/0037270 A1 | 2/2013 | DiFoggio | |
| 2013/0081879 A1 | 4/2013 | Ward et al. | |
| 2013/0175036 A1 | 7/2013 | Hausot | |
| 2014/0131033 A1 | 5/2014 | Galvan-Sanchez | |
| 2016/0273292 A1 | 9/2016 | Morgan | |
| 2016/0326866 A1 | 11/2016 | Swett | |
| 2019/0129056 A1 | 5/2019 | Rasmus et al. | |
| 2019/0277806 A1 | 9/2019 | Huang | |
| 2020/0003599 A1 | 1/2020 | Theuveny et al. | |
| 2020/0088020 A1 | 3/2020 | Batarseh et al. | |
| 2021/0340859 A1 | 11/2021 | Al-Huwaider | |
| 2022/0042898 A1 * | 2/2022 | Zhao | G01N 33/24 |

FOREIGN PATENT DOCUMENTS

| | | |
|---|---|---|
| WO | WO 2008150825 | 12/2008 |
| WO | WO 2014012781 | 1/2014 |

OTHER PUBLICATIONS

"Multiple Array Production Suite (MAPS)," Proactive Diagnostic Services, Well Integrity Diagnostic Specialists, Brochure, 2 pages, Dec. 2021.

Abernethy, "Production increase of heavy oils by electromagnetic heating," Journal of Canadian Petroleum Technology, Jul.-Sep. 1976, 8 pages.

Akinlolu, "Capillary Pressure Determination Using the Micropore Membrane Technique," A Thesis Submitted to the Graduate Faculty of Texas Tech University in Partial Fulfillment of the Requirements for the Degree of Master of Science in Petroleum Engineering, May 2012.

Al-Bulushi et al., "Capillary Pressure Corrections, Quality Control and Curve Fitting Workflow," IPTC-19514-MS, International Petroleum Technology Conference, 2019, 25 pages.

Almansour and Al-Bassaz, "Physical and Chemical characterization and evaluation of organic matter from tar-mat samples: Case Study of Kuwaiti Carbonate Reservoir," Journal of Chemical Technology App 1:1, Sep. 2017, 12 pages.

Alomair et al., "Viscosity Prediction of Kuwaiti Heavy Crudes at Elevated Temperatures," SPE 150503, Society of Petroleum Engineers (SPE), presented at the SPE Heavy Oil Conference and Exhibition, Kuwait, Dec. 12-14, 2011, 18 pages.

aqua-calc.com [online], "Volume of liquid ammonia," available on or before Nov. 1, 2014 via Internet Archive, Wayback Machine URL <https://web.archive.org/web/20141101074746/https://www.aqua-calc.com/calculate/weight-to-volume/substance/liquid-blank-ammonia>, retrieved on Sep. 17, 2021, retrieved from URL <https://www.aqua-calc.com/calculate/weight-to-volume/substance/liquid-blank-ammonia>, 3 pages.

araner.com [online], "What makes combined cycle power plants so efficient," 2021, retrieved on Sep. 17, 2021, retrieved from URL <https://www.araner.com/blog/combined-cycle-power-plants>, 10 pages.

bakerhughes.com [online] "VACS G2 system," Baker Hughes, available on or before Oct. 5, 2020, retrieved on Jan. 7, 2021, retrieved from URL <https://www.bakerhughes.com/wellbore-cleanup/vacs-g2-system>, 5 pages.

bakerhughes.com [online] "Vectored annular cleaning system (VACS) technology," available on or before Oct. 5, 2020, retrieved on Jan. 7, 2021, retrieved from URL https://www.bakerhughes.com/wellbore-cleanup/vectored-annular-cleaning-system-vacs-technology, 4 pages.

Bauldauff et al., "Profiling and quantifying complex multiphase flow," Oilfield Review, Autumn 2004, 10 pages.

Bermudez et al., "Assisted Extra Heavy Oil Sampling by Electromagnetic Heating," SPE 171073-MS, Society of Petroleum Engineers (SPE), presented at the SPE Heavy and Extra Heavy Oil Conference—Latin American, Colombia, Sep. 24-26, 2014, 13 pages.

Bhushan et al., "Advanced Logging Applications for Brownfield Optimization," Presented at the International Petroleum Technology Conference held in Dubai, U.A.E., Dec. 4-6, 2007, 7 pages.

Bockmiller et al., "University of California strategies for decarbonization: Replacing Natural Gas TomKat Natural Gas Exit Strategies Working Group Report to the TomKat Foundation," University of California, Feb. 2018, 101 pages.

Bristow et al., "Comparison of Single and Dual Probes for Measuring Soil Thermal Properties With Transient Heating," Soil Research, 1994, 32 (3): 447.

Bristow et al., "Measurement of Soil Thermal Properties with a Dual-Probe Heat-Pulse Technique," Soil Sci. Soc. Am. J. 58:1288-1294, Sep. 1994, 7 pages.

(56) References Cited

OTHER PUBLICATIONS

Ciesche, "Mercury Porosimetry," Handbook of Porous Solids, 2002, 43 pages.
Collodi et al., "Hydrogen Production via Steam Reforming with CO2 Capture," Chemical Engineering Transactions, Apr. 2010, 19:37-42, 6 pages.
Eyvazzadeh et al., "An Innovative Application to Reduce Petrophysical Uncertainty in Reservoir Monitoring: Case Studies from Giant Saudi Arabian Fields," SPE 97519, Society of Petroleum Engineers (SPE), SPE International Improved Oil Recovery Conference in Asia Pacific, Dec. 5-6, 2005.
glossary.oilfield.slb.com [online], "Distributed temperature log," retrieved from URL <https://www.glossary.oilfield.slb.com/en/Terms/d/distributed temperature_log.aspx>, retrieved on Feb. 12, 2020, available on or before 2020, 1 page.
halliburton.com, [online], "CoreVault System," available on or before 2020, retrieved on Nov. 9, 2020, retrieved from URL <https://www.halliburton.com/en-US/ps/wireline-perforating/wireline-and-perforating/open-hole-logging/sidewall-coring/corevault.html>, 2 pages.
horizontalwireline.com [online], "Multi-arm Caliper MAC 40," retrieved from URL <https://horizontalwireline.com/wp-content/uploads/2014/09/AHWS-Multi-Arm_Caliper.pdf>, retrieved on Feb. 12, 2020, available on or before 2014, 2 pages.
Huang, "Impact of rising natural gas prices on U.S. ammonia supply," A Report from the Economic Research Service, United States Department of Agriculture, Aug. 2007, 19 pages.
ipieca.org [online], "Open cycle gas turbines," Feb. 2014, retrieved on Sep. 17, 2021, retrieved from URL <https://www.ipieca.org/resources/energy-efficiency-solutions/power-and-heat-generation/open-cycle-gas-turbines/>, 12 pages.
JPT Staff, "Techbits: Enhancing Production in Russia's Oil and Gas Fields," SPE-0706-0024-JPT, J Pet Technol, 2006, 58(07): 24-25, 2 pages.
Kelder et al., "Expanding advanced production logging operations to short radius horizontal wells," SPE 93526, Society of Petroleum Engineers (SPE), presented at the 14th SPE Middle East Oil & Gas Show and Conference, Bahrain International Exhibition Centre, Bahrain, Mar. 12-15, 2005, 7 pages.
Kuchuk et al., "Horizontal Well Performance Evaluation Tools and Techniques," SPE 48853, Society of Petroleum Engineers, 1998, 16 pages.
Lenn, "Horizontal Well Performance Evaluation and Fluid Entry Mechanisms," SPE-49089-MS, Society of Petroleum Engineers, Sep. 1998, 13 pages.
Liu, "Acoustic Properties of Reservoir Fluids," A Dissertation Submitted to the Department of Geophysics and Committee on Graduate Studies of Stanford University in Partial Fulfillment of the Requirements for the Degree of Doctor of Philosophy, Jun. 1998, 111 pages.
Lu et al., "An Improved Model for Predicting Soil Thermal Conductivity From Water Content at Room Temperature," Soil Science Society of America Journal, 2007, 71: 8-14.
Ma et al., "Cased-hole reservoir saturation monitoring in mixed-salinity environments—A new integrated approach," SPE 92426, Society of Petroleum Engineers (SPE), presented at the 14th SPE Middle East Oil & Gas Show and Conference, Bahrain, Mar. 12-15, 2005, 10 pages.
Ma et al., "Dynamic petrophysics—applications of time-lapse reservoir monitoring in Saudi Arabia," SPE 95882, Society of Petroleum Engineers (SPE), presented at the 2005 SPE Annual Technical Conference and Exhibition, Dallas, Texas, Oct. 9-12, 2005, 8 pages.
Ma et al., "Resolving the mixed salinity challenges with a methodology developed from pulsed neutron capture gamma ray spectral measurements," SPE 170608, Society of Petroleum Engineers (SPE), presented at the SPE Annual Technical Conference and Exhibition, Amsterdam, The Netherlands, Oct. 27-29, 2014, 12 pages.
McCoy et al., "Analyzing Well Performance VI," Southwestern Petroleum Short Course Association, Lubbock, 1973, 9 pages.

metergroup.com [online], "Thermal Properties: Why the TEMPOS method outperforms other techniques," retrieved from URL <https://www.metergroup.com/environment/articles/thermal-properties-transient-methodoutperforms-techniques/>, retrieved on Feb. 12, 2020, available on or before 2020, 6 pages.
Mohamed et al., "Leak Detection by Temperature and Noise Logging," Society of Petroleum Engineers, Abu Dhabi International Petroleum Conference and Exhibition, Nov. 11-14, 2012, Abu Dhabi, UAE, abstract retrieved from URL <https://archive.is/20130628032024/http://www.onepetro.org/mslib/servlet/onepetropreview#selection-191.0-191.96>, retrieved on Feb. 12, 2020, 2 pages, Abstract Only.
Moses, "Geothermal Gradients," Drilling & Production Practice, Core Lab. Inc., Dallas, Texas, 1961, 7 pages.
oilproduction.net [online], "Acoustic Velocity for Natural Gas," retrieved on Jan. 7, 2021, URL <http://oilproduction.net/files/Acoustic%20Velocity%20for%20Natural%20Gas.pdf>, 6 pages.
powerengineeringint.com [online], "Gas turbines breaking the 60% efficiency barrier," Power Engineering International, May 2010, retrieved on Sep. 21, 2021, retrieved from URL <https://www.powerengineeringint.com/coal-fired/equipment-coal-fired/gas-turbines-breaking/>, 6 pages.
Rajesh et al., "Thermal efficiency of combined cycle power plant," International Journal of Engineering and Management Research, Jun. 2018, 8(3):229-234, 7 pages.
Shagdar et al., "Process analysis of solar steam reforming of methane for producing low-carbon hydrogen," Royal Society of Chemistry, 2020, 10:12582, 16 pages.
slb.com [online] "Well Scavenger," Schlumberger, available on or before Aug. 3, 2020, via Internet Archive: Wayback Machine URL <http://web.archive.org/web/20200803130523/https://www.slb.com/completions/fluids-and-tools/wellbore-cleaning-tools/debris-recovery-tools/well-scavenger-vacuum-debris-removal-tool>, retrieved on Jan. 12, 2021, URL <https://www.slb.com/completions/fluids-and-tools/wellbore-cleaning-tools/debris-recovery-tools/well-scavenger-vacuum-debris-removal-tool>, 5 pages.
slb.com [online], "PS Platform, Production services platform," retrieved from URL <https://www.slb.com/-/media/files/production/product-sheet/ps_platform_ps.ashx>, retrieved on Feb. 12, 2020, available on or before 2014, 3 pages.
Supple, "Units & Conversions Fact Sheet," Massachusetts Institute of Technology Energy Club, Apr. 2007, 2 pages.
Thomas et al., "Determination of Acoustic Velocities for Natural Gas," SPE 2579, Society of Petroleum Engineers (SPE), Journal of Petroleum Technology, Jul. 1970, 22(7):889-895.
Wang et al., "Acoustic Velocities in Petroleum Oils," SPE 18163 MS/ SPE 18163 PA, Society of Petroleum Engineers (SPE), presented at the SPE Annual Technical Conference and Exhibition, Oct. 2-5, 1988, 15 pages.
web.mit.edu [online], "8.7 Combined cycles in stationary gas turbine for power production," available on or before May 11, 2021, via Internet Archive, Wayback Machine URL <https://web.archive.org/web/20120915000000*/http://web.mit.edu/16.unified/www/SPRING/thermodynamics/notes/node67.html>, retrieved on Sep. 16, 2021, retrieved from URL <http://web.mit.edu/16.unified/www/SPRING/thermodynamics/notes/node67.html>, 3 pages.
Webb, "An Introduction to the Physical Characterization of Materials by Mercury Intrusion Porosimetry with Emphasis on Reduction and Presentation of Experimental Data," Micromeritics Instrument Corp., Jan. 2001.
Welch et al., "Improving the flexibility and efficiency of gas turbine-based distributed power plants," Power Engineering, Sep. 2015, 14 pages.
Wesenberg, "Gas heated steam reformer modelling," Doctoral thesis for the degree of doktor ingenior Trondheim, Norwegian University of Science and Technology, Apr. 2006, 210 pages.
wildcatoiltools.com [online] "HydroVortex," Wildcat Oil Tools, available on or before Oct. 5, 2020, retrieved on Jan. 12, 2021, retrieved from URL <https://www.wildcatoiltools.com/hydrovortex>, 5 pages.

(56) References Cited

OTHER PUBLICATIONS

Wilhelms and Larter, "Origin of tar mats in petroleum reservoirs Part II: Formation mechanisms for tar mats," Marine Petroleum Geology 11:4, Aug. 1994, 15 pages.

* cited by examiner

SINGLE STAGE MICP MEASUREMENT METHOD AND APPARATUS

TECHNICAL FIELD

This disclosure relates to a single stage high pressure mercury injection capillary pressure measurement system for measuring samples at high pressures and at low pressures.

BACKGROUND

Mercury Injection Capillary Pressure (MICP) experiments are one of several methods to obtain capillary pressure vs saturation curves which helps to understand fluid distribution and heterogeneity of a rock sample from a reservoir to predict the reservoir performance. Existing machines that conduct the high-pressure experiment have two stages (low pressure and high pressure) where a penetrometer is manually removed from the low-pressure stage to be installed in the high-pressure stage, during a complete test.

SUMMARY

In certain aspects, a mercury injection capillary pressure (MICP) measurement apparatus includes a sample sub-assembly. The sample sub-assembly has casing having walls defining an interior volume, a penetrometer arranged in the casing, the penetrometer having walls defining a sample volume, an annular space defined between the walls of the casing and the walls of the penetrometer, and a common chamber fluidly connected to the annular space by a fluid line and to the sample volume of the penetrometer by a tubing. The measurement apparatus also includes a transducer sub-assembly fluidly connected to the sample sub-assembly via the common chamber. The transducer sub assembly includes a plurality of high-pressure transducers configured to measure a pressure above 30 psi and a plurality of low-pressure transducers configured to measure a pressure below 30 psi. The measurement apparatus further includes a hydraulic intensifier fluidly connected to the common chamber and configured to apply a high pressure to the annular space, and a gas tank in fluid connection with the common chamber and configured to apply a low pressure to the sample volume of the penetrometer.

In some embodiments, the apparatus includes a mercury source and mercury chamber. The mercury chamber is fluidly connected to the common chamber. Some mercury sources are fluidly connected to the sample volume of the penetrometer.

The plurality of high pressure transducers can include a transducer configured to measure a pressure between 30 psi and 100 psi, a transducer configured to measure a pressure between 30 psi and 130 psi, a transducer configured to measure a pressure between 100 psi and 500 psi, a transducer configured to measure a pressure between 100 psi and 600 psi, a transducer configured to measure a pressure between 500 psi and 5,000 psi, a transducer configured to measure a pressure between 500 psi and 6,000 psi, a transducer configured to measure a pressure between 5,000 psi and 60,000 psi, or any combination thereof.

The plurality of low-pressure transducers can include a transducer configured to measure a pressure between 0 psi and 0.7 psi, a transducer configured to measure a pressure between 0.5 psi and 1.5 psi, a transducer configured to measure a pressure between 1 psi and 7 psi, a transducer configured to measure a pressure between 5 psi and 15 psi, a transducer configured to measure a pressure between 10 psi and 40 psi, or any combination thereof.

In some apparatuses, each of the low pressure transducers in the plurality of low pressure transducers are connected to the chamber via a low pressure fluid line of a plurality of low pressure fluid lines. A low pressure threshold valve may be arranged on each of the low pressure fluid lines and can be configured to close at a threshold pressure.

In some apparatuses, each of the high pressure transducers in the plurality of high pressure transducers are connected to the chamber via a high pressure fluid line of a plurality of high pressure fluid lines. A high pressure threshold valve may be arranged on each of the high pressure fluid lines and can be configured to close at a threshold pressure.

The sample volume can be configured to contain a porous medium sample. The porous medium sample can be a consolidated rock sample, an unconsolidated rock sample, a soil sample, a powder sample, or a combination thereof.

In some embodiments, the apparatus also includes a first pressure transducer arranged in the common chamber and a second pressure transducer arranged in the annular space of the casing.

In some embodiments, the apparatus also includes a valve arranged on the fluid line.

In some embodiments, the apparatus also includes a vacuum pump fluidly connected to the common chamber.

In certain aspects, a method to test a rock sample in a single stage MICP apparatus, the method includes applying, in a stage, a low pressure to a sample volume of a penetrometer in a single stage MICP apparatus; and applying, in the same stage, a high pressure to the sample volume of the penetrometer in the single stage MICP apparatus.

The step of applying, in the stage, the low pressure to the sample volume of a penetrometer in the single stage MICP apparatus can include controlling a pressure by flowing a gas from a gas cylinder to the sample volume.

In some methods, applying, in the stage, the low pressure to the sample volume of a penetrometer in the single stage MICP apparatus includes increasing the pressure from 0 psi to 40 psi over a predetermine period of time.

In some embodiments, applying, in the stage, the low pressure to the sample volume of a penetrometer in the single stage MICP apparatus includes measuring a mercury level in the apparatus. In some cases applying, in the same stage, the high pressure to the sample volume of a penetrometer in the single stage MICP apparatus includes measuring a mercury level in the apparatus. The method can include generating, by a controller of the apparatus, a continuous MICP curve.

In some cases, applying, in the same stage, the high pressure to the sample volume of a penetrometer in the single stage MICP apparatus includes controlling a pressure by flowing a gas from an hydraulic intensifier.

In some methods, applying, in the same stage, the high pressure to the sample volume of a penetrometer in the single stage MICP apparatus includes increasing the pressure from 30 psi to 60,000 psi over a predetermine period of time.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

The single stage mercury injection capillary pressure system is disclosed for measuring a capillary pressure vs saturation curve (e.g., a capillary pressure curve) of a porous medium, such as a rock sample from a reservoir. The apparatus generates capillary pressure curves that are used to understand fluid distribution and heterogeneity of a rock sample from a reservoir to predict the reservoir performance. The apparatus measures pressures between a range of 0 pounds per square inch (psi) to 60,000 psi continuously, without removing the sample from the penetrometer of the apparatus. The apparatus includes a low pressure fluid circuit for applying a pressure between 0 psi and 40 psi to the rock sample and a high pressure fluid circuit for applying a pressure between 30 psi and 60,000 psi to the rock sample. The low pressure fluid circuit and the high pressure fluid circuit are each fluidly connected to a sample sub-assembly, specifically to a common chamber of the sample sub-assembly. The sample subassembly also includes a sealed casing connected to the common chamber and a penetrometer arranged in the sealed chamber for containing the rock sample. This configuration can test the rock sample at a variety of capillary pressures without removing the sample from a testing volume, thereby generating continuous capillary pressure curve graphs and producing more accurate data.

Figure 1:
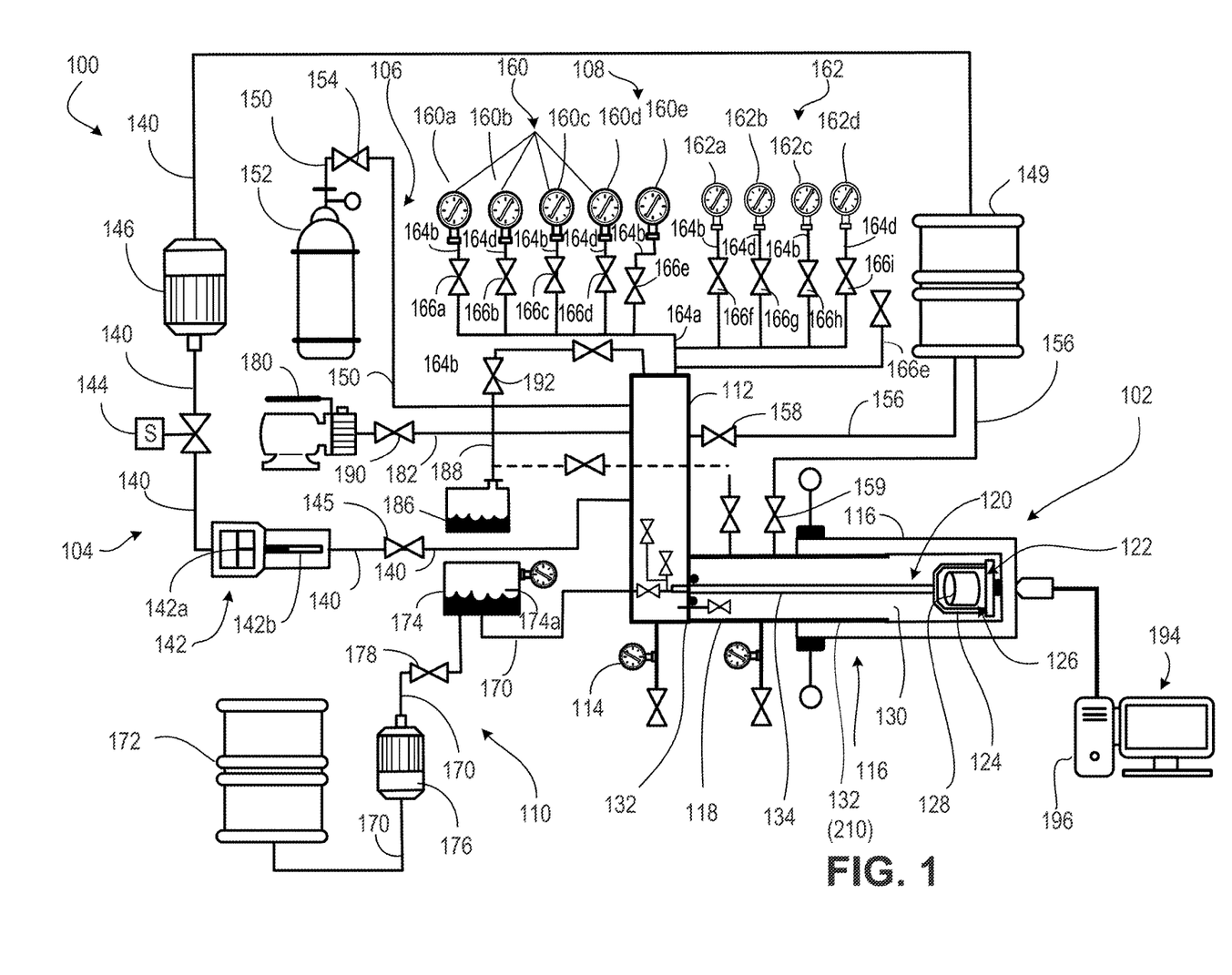
FIG. 1 is a schematic view of a single stage MICP measurement apparatus.

FIG. 1 is a schematic view of a single stage MICP measurement apparatus 100. The apparatus 100 includes a sample sub assembly 102, a high pressure fluid circuit 104, a low pressure fluid circuit 106, a transducer sub-assembly 108, and a mercury sub-assembly 110. The sample sub assembly 102 includes a common chamber 112 fluidly connected to the high pressure fluid circuit 104, the low pressure fluid circuit 106, the transducer sub-assembly 108, and the mercury sub-assembly 110, such that, depending on valve positions, the common chamber shares a pressure with the high pressure fluid circuit 104, the low pressure fluid circuit 106, the transducer sub-assembly 108, and/or the mercury sub-assembly 110. A first pressure transducer 114 is arranged in or disposed on the common chamber 112. The first pressure transducer 114 includes a transceiver (not shown) operable to transmit first pressure data that contains the pressures measured in the common chamber 112. The sample sub-assembly 102 also includes a casing 116 having walls 118 defining an interior volume 120. A penetrometer 122 of the sample sub-assembly 102 is arranged in the casing 116. The penetrometer 122 has walls 124 that define a sample volume 126. A porous medium sample is arranged in the sample volume 126. In the system 100 the porous medium sample is a rock sample 128, for example a rock sample from a reservoir. In some system, the porous medium sample is a soil sample, a powder sample, a consolidated rock sample, unconsolidated rock sample, or a combination thereof. The rock sample 128 is arranged in the sample volume 126 for testing the capillary pressure of the rock sample 128 at both low pressures (0 psi to 30 psi) and high pressures (30 psi to 60,000 psi). An annular space 130 defined between the walls 118 of the casing 116 and the walls 124 of the penetrometer 122. The common chamber 112 is fluidly connected to the annular space 130 by a fluid line 132 and to the sample volume 126 of the penetrometer 122 by a tubing 134. The tubing 134 has a conductive coating on an exterior surface facing the annular space 130. The tubing 134 forms a cylindrical capacitor, of which a capacitance can be measured by an electric probe. The capacitance of the tubing 134 is a function of the area of the conductors, the dielectric constant of the insulator and other physical parameters of the tubing. In use, mercury, in the tubing 134 moves into a sample in the sample volume 126, thereby changing the amount of mercury that contacts the tubing walls. The capacitance measured varies as the amount of mercury contacting the tubing walls changes. In some cases, this capacitance is measured at a stem of the tubing. The sample sub-assembly 102 is described in further detail with reference to FIG. 2.

The high-pressure fluid circuit 104 includes a high-pressure fluid line 140 on which lies a hydraulic intensifier 142, a solenoid valve 144, and a hydraulic pump 146. The fluid line 140 is fluidly connected to the common chamber 112, the annular space 130 via the fluid line 132, and the sample volume 126 via the tubing 134. A high pressure valve 145 controls the fluidic connection between the high pressure fluid circuit 104 and the sample sub-assembly 102.

The hydraulic intensifier 142 is configured to apply a high pressure to the annular space 130 and tubing 134, simultaneously during use. The hydraulic intensifier 142 includes a low pressure section 142a and a high pressure section 142b. The low pressure section 142a receives low pressure fluid from the fluid source 149 and a piston presses the fluid in the low pressure section 142a to the high pressure section 142b. The high pressure section 142b has a smaller cross sectional area than the low pressure section 142a such that the pressure of the fluid increases as the fluid is pressed by the piston from the low pressure section 142a to the high pressure section 142b. The pressure intensifier generates pressures between about 0 psi and about 60,000 psi (e.g., between 30 psi and 60,000 psi). The output pressure from the high pressure section 142b is controlled by a ratio of the cross sectional area of the low pressure section 142a to the cross sectional area of the high pressure section 142b. The larger the ratio, the higher the pressure intensification. Generally, intensifiers have pressure ratios ranging up to 50. The hydraulic pump 146 draws fluid from a hydraulic fluid source 149 fluidly connected to the high pressure fluid circuit 104.

The low-pressure fluid circuit 106 includes a low-pressure fluid line 150 fluidly connecting a fluid source 152 (e.g., a pressurized gas cylinder, pressurized gas tank) to the common chamber 112. A low pressure valve 154 controls the fluidic connection between the low pressure circuit 106 and the sample sub-assembly 102. The fluid source 149, for holding hydraulic fluid, is also connected directly to the common chamber 112 and casing 116 by hydraulic fluid lines 156. The fluid connection between the fluid source 149 and the common chamber 112 is controlled by a first hydraulic fluid valve 158. The fluid connection between the fluid source 149 and the annular space 130 of the casing 116 is controlled by a second hydraulic fluid valve 159.

The low-pressure fluid circuit 106 includes a low-pressure fluid line 150 fluidly connecting a fluid source 152 (e.g., a pressurized gas cylinder, pressurized gas tank) to the common chamber 112. A low pressure valve 154 controls the fluidic connection between the low pressure circuit 106 and the sample sub-assembly 102. The fluid source 149, for holding hydraulic fluid, is also connected directly to the common chamber 112 and casing 116 by a hydraulic fluid lines 156. The fluid connection between the fluid source 149 and the common chamber 112 is controlled by a first hydraulic fluid valve 158. The fluid connection between the fluid source 149 and the annular space 130 of the casing 116 is controlled by a second hydraulic fluid valve 159.

The transducer sub-assembly 108 includes multiple low-pressure transducers 160 configured to measure a pressure up to 40 psi and multiple of high-pressure transducers 162 configured to measure a pressure above 30 psi. The multiple low pressure transducers 160 include a first low pressure transducer 160a, a second low pressure transducer 160b, a third low pressure transducer 160c, a fourth low pressure transducer 160d, and a fifth low pressure transducer 160e. The multiple high pressure transducers 162 include a first high pressure transducer 162a, a second high pressure transducer 162b, a third high pressure transducer 162c, and a fourth high pressure transducer 162d. The transducer sub-assembly 108 is fluidly connected to the common chamber 112 by a pressure fluid line 164.

The transducer sub-assembly 108 includes a plurality of threshold valves 166 arranged on the pressure fluid line 164 between the pressure transducers 160, 162 and the common chamber 112. The threshold valves 166 dissect the pressure fluid line 164 into a first portion 164a that connects to the common chamber 112 and a second portion 164b between the threshold valve 166 and the transducers 160, 162. The first section 164a of the pressure fluid line 164 shares the pressure of the common chamber 112. The second portion 164b of the pressure fluid line 164 shares the pressure of the common chamber 112 when the threshold valves are open.

The first low pressure transducer 160a is capable of measuring a pressure range between 0 psi and 0.7 psi. The second low pressure transducer 160b is capable of measuring a pressure range between 0.5 psi and 1.5 psi. The third low pressure transducer 160c is capable of measuring a pressure range between 1 psi and 7 psi. The fourth low pressure transducer 160d is capable of measuring a pressure range between 5 psi and 15 psi. The fifth pressure transducer 160e is capable of measuring a pressure range between 10 psi and 40 psi. The first high pressure transducer 162a is capable of measuring a pressure range between 30 psi and 130 psi. The second high pressure transducer 162b is capable of measuring a pressure range between 100 psi and 600 psi. The third high pressure transducer 162c is capable of measuring a pressure range between 500 psi and 6,000 psi. The fourth high pressure transducer 162d is capable of measuring a pressure range between 5,000 psi and 60,000 psi.

The multiple threshold valves 166 includes a first threshold valve 166a, a second threshold valve 166b, a third threshold valve 166c, a fourth threshold valve 166d, a fifth threshold valve 166e, a sixth threshold valve 166f, a seventh threshold valve 166g, an eighth threshold valve 166h, and a ninth threshold valve 166i. Some apparatus include less than eight threshold valves or more than eight threshold valves. Each threshold valve 166 is configured to close at a predetermined pressure threshold. In the transducer sub-assembly 108, the threshold valves 166 close at different threshold pressures. In some apparatuses, the pressure thresholds are the same.

The first threshold valve 166a is arranged on the pressure fluid line 164, downstream of the first low pressure transducer 160a. The second threshold valve 166b is arranged on the pressure fluid line 164, downstream of the second low pressure transducer 160b. The third threshold valve 166c is arranged on the pressure fluid line 164, downstream of the third low pressure transducer 160c. The fourth threshold valve 166d is arranged on the pressure fluid line 164, downstream of the fourth low pressure transducer 160d. The fifth threshold valve 166e is arranged on the pressure fluid line 164, downstream of the fifth low pressure transducer 160e.

The sixth threshold valve 166f is arranged on the pressure fluid line 164, downstream of the first high pressure transducer 162a. The seventh threshold valve 166g is arranged on the pressure fluid line 164, downstream of the second high pressure transducer 162b. The eighth threshold valve 166h is arranged on the pressure fluid line 164, downstream of the third high pressure transducer 162c. The ninth threshold valve 166i is arranged on the pressure fluid line 164, downstream of the fourth high pressure transducer 162d. In some transducer sub-assemblies, a threshold valve is not arranged the fluid line to separate the first high pressure transducer, the second high pressure transducer, the third high pressure transducer, and/or the fourth high pressure transducer from the common chamber 112.

If the pressure in the first section 164a of the pressure fluid line 164 (and thereby the pressure of the common chamber 112) reaches or exceeds the threshold of a threshold valve 166, the threshold valve closes and isolates the pressure transducer 160, 162 from the common chamber 112. For example, the first threshold valve 166a has a pressure threshold of about 0.5 psi (e.g., about 0 psi to about 0.6 psi). The second threshold valve 166b has a pressure threshold of about 1 psi (e.g., about 0.5 psi to about 1.1 psi). The third threshold valve 166c has a pressure threshold of about 5 psi (e.g., about 1 psi to about 6 psi). The fourth threshold valve has a pressure threshold of about 10 psi (e.g., about 5 psi to about 12 psi). The fifth threshold valve 166e has a pressure threshold of about 30 psi (e.g., about 10 psi to about 35 psi). The sixth threshold valve 166f has a pressure threshold of about 100 psi (e.g., about 30 psi to about 110 psi). The seventh threshold valve 166g has a pressure threshold of about 500 psi (e.g., about 100 psi to about 600 psi). The eighth threshold valve 166h has a pressure threshold of about 5000 psi (e.g., about 500 psi to about 6000 psi). The ninth threshold valve 166i has a pressure threshold of about 60,000 psi (e.g., about 5000 psi to about 60,000 psi), the maximum allowed pressure of the tests.

The transducer sub-assembly 108 is able to automatically isolate a pressure transducer 160, 162 that may be damaged by a high (or low) pressure. For example, the first low pressure transducer for measuring pressures between 0 psi and 0.6 psi could be damaged if exposed to a high pressure of 20,000 psi. In the transducer sub-assembly, the first threshold valve, automatically closes at the predefined pressure of 0.5 psi (e.g., 0.4 psi, 0.55 psi, 0.6 psi, 0.7 psi, or 1 psi), thereby preventing the first low pressure transducer from experiencing damaging pressures. Some threshold valves have pressure threshold that are higher than the minimum measured pressure of the adjacent pressure transducer. Such a configuration can generate overlapping measurement data, (e.g., pressure measurements generated by two adjacent pressure transducers).

The apparatus also includes the mercury sub-assembly 110 (mercury fluid circuit) that includes a mercury fluid line 170 fluidly connecting a mercury source 172 to a mercury chamber 174. The mercury fluid line 170 also fluidically connects the mercury chamber 174 to the common chamber 112 and sample volume 126 via the tubing 134. The mercury sub-assembly 110 (mercury fluid circuit) also includes a pump 176 for pumping mercury from the mercury source 172 to the mercury chamber 174. In use, the mercury pump 176 conveys mercury into the mercury chamber 174 to a predetermined volume or level (for example, a volume or level higher than the penetrometer 122 or sample volume 126) so that mercury moves to from the chamber 174 to the penetrometer 122 by the hydrostatic pressure of the mercury, until the mercury fills the penetrometer 122 and sample volume 126. The fluid connection between the mercury source 172 and mercury pump 176 to the mercury chamber 174 is controlled by a mercury valve 178. In use, a mercury level, or change in mercury level, in the mercury chamber 174 is indicative of the amount of mercury in the sample sub-assembly 102.

The apparatus 100 further includes a vacuum pump 180 connected to the common chamber 112 via a vacuum fluid line 182 and a fluid level indicator 186 fluidly connected to the common chamber 112 and casing 116 via indicator fluid lines 188. The vacuum fluid line 182 includes a valve 190 that closes or opens to control the fluidic connection between the common chamber 112 and the vacuum pump 180. The indicator fluid line 188 includes a first indicator fluid valve 192 that closes or opens to control the fluidic connection between the common chamber 112 and the fluid level indicator 186 The indicator fluid line 188 includes a second indicator fluid valve 193 that closes or opens to control the fluidic connection between the annular space 130 of the casing 116 and the fluid level indicator 186. In some apparatus, the indicator fluid line includes multiple valves.

A computer system 194 of the apparatus includes a controller 196 one or more processors, a computer-readable medium storing instructions executable by the one or more processors to perform operations. The controller 196 is connected to each valve in the system and each pump in the system so that the controller controls the position of each valve (e.g., open or closed) and controls the pump rates of the pumps. The computer system 194 also includes a display 198 for displaying the capillary pressure curve and for gather input from an operator.

Figure 2:
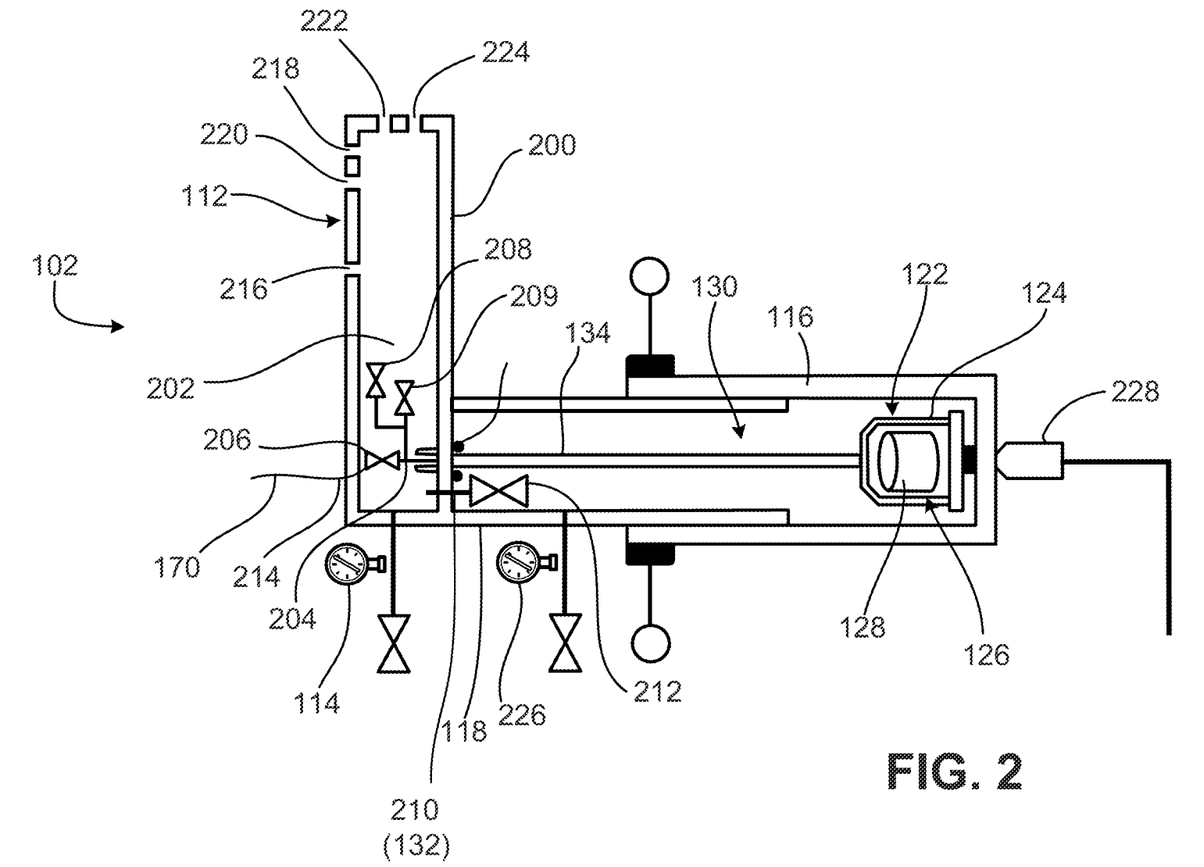
FIG. 2 is a view of the sample sub-assembly of the apparatus.

FIG. 2 is a view of the sample sub-assembly 102 of the apparatus 100. The common chamber 112 includes walls 200 defining an interior volume 202. The common chamber 112 is used to transfer pressures generated by the high pressure fluid circuit 104 or low pressure fluid circuit 106 to the correct locations in the annular space 130 and/or sample volume 126. The common chamber 112 also transfers fluids to the annular space 130 and the sample volume 126. Some common chambers are sized so as to not extend past a top wall of the casing. This configuration can minimize hydrostatic pressure from hydraulic fluid chamber.

The common chamber 112 includes a connection tubing 204 that fluidly connects to the mercury fluid line 170 by a first connection valve 206 and to the interior volume 202 of the common chamber by a second connection valve 208 and a third connection valve 209. The second connection valve 208 allows movement of a fluid into the penetrometer tubing 134 and out of the penetrometer tubing 134. The third connection valve 209 is a check vale that permits movement of a fluid into the penetrometer tubing 134 and prevents movement of a fluid out of the penetrometer tubing 134. The connection tubing 204 extends from the first and second connection valves 206, 208 to connect to the tubing 134, such that when the first connection valve is open, mercury from the mercury chamber 174 can flow into the sample volume 126 and when the second connection valve 208 is open, fluid in the interior volume 202 of the common chamber can flow into the sample volume 126. When the second connection valve 208 is open, the pressure in the interior volume of the common chamber 112 is applied to the sample volume 126.

The sample sub-assembly 102 further includes an annular tubing 210 that fluidly connects the interior volume 202 of the common chamber 112 to the annular space 130 defined in the casing 116. An annular valve 212 is arranged on the annular tubing 210 to control the fluid connection between the interior volume 202 of the common chamber 112 and the annular space 130 of the casing 116. When the annular valve 212 is open, the interior volume 202 of the common chamber 112 and the annular space 130 of the casing 116 share a pressure.

The walls 200 of the common chamber 112 define a plurality of inlets connecting the interior volume 202 and/or the connection tubing 204 to other subassemblies or components in the apparatus. The walls 200 define a mercury tubing inlet 214 for receiving the mercury tubing 170, a high pressure inlet 216 for receiving the high pressure fluid line 140, a low pressure inlet 218 for receiving the low pressure fluid line 150, a vacuum inlet 220 for receiving the vacuum fluid line 182, a fluid indicator inlet 222 for receiving the indicator fluid line 188, and a transducer inlet 224 for receiving the first portion 164a of the pressure fluid line 164.

A second transducer 226 is arranged in or disposed on the casing such that the second pressure transducer measures the pressure in the annular space 130. An electric plug 228 extends through the walls 118 of the casing to connect to the penetrometer 122 to connect the penetrometer 122 to the computer system 194. The plug 228 induces an electric current to the tubing 134, which has a conductive coating. The plug 228 also measures the electrical capacitance of the tubing 134 as mercury moves through the tubing 134 and sample.

Figure 3:
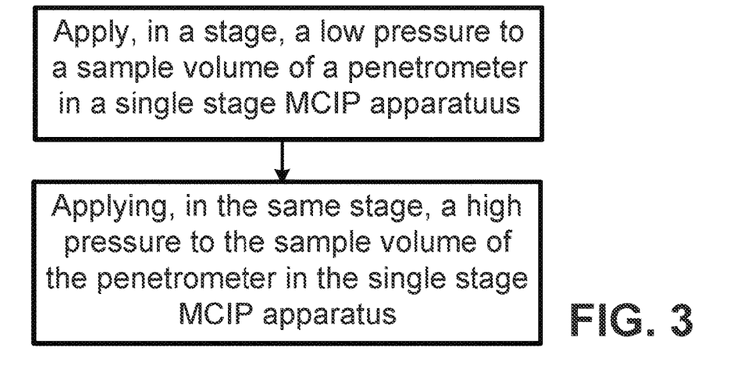
FIG. 3 is a flowchart of a method of operating a single stage MICP measurement apparatus.

FIG. 3 is a flowchart of a method 250 of operating a single stage MICP measurement apparatus. The method 250 is described with reference to the apparatus 100, however, the method may be used with any applicable apparatus or system.

Initially, all valves in the system are closed and a rock sample 128 is loaded into the penetrometer 122 and the penetrometer 122 is closed to form the sample volume 126. The penetrometer is inserted into the casing 116 and the connected to the tubing 134 so that the sample volume 126 is fluidly connected to the connection tubing 204. The casing 116 is closed to form the annular space 130 and electric plug 228 is connected to the penetrometer 122 to electrically and operable connect the computer system 194 to the penetrometer 122. The penetrometer 122 is configured to measure mercury movement inside the tubing 134.

Prior to testing the rock sample 128, the sample volume 126, the common chamber 112, the mercury chamber 174, and the annular space 130 must be under vacuum pressure. To do this, the vacuum valve 190 is opened to fluidly connect the interior volume 202 of the common chamber 112 to the vacuum pump 180. The threshold valves 166 of the transducers sub-assembly 108 are opened to monitor the pressure in the common chamber 112 and the annular valve 212 is opened. The first transducer 114 and second transducer 226 also monitor the pressure in the common chamber 112 and the annular space 130, respectively. The transducers 114, 160, 162, 226 transmit pressure data to the computer system 194 containing the pressure measurements taken by each transducers 114, 160, 162, 226. The second connection valve 208 in the common chamber 112 is opened to fluidly connect the interior volume 120 of the common chamber 112 with the tubing 134 and sample volume 126 of the penetrometer 122. The first connection valve 206 is opened to fluidly connect the mercury chamber 174 with the interior volume 202 of the common chamber 112 via the open second connection valve 208. The annular valve 212 is also opened to fluidly connect the annular space 130 with the interior volume 202 of the common chamber 112. At this point, the interior volume 202 of the common chamber shares a pressure with the mercury chamber 174, the annular space 130, the sample volume 126, the transducer sub-assembly 108, and the vacuum fluid line 182. The vacuum pump 180 adjust the pressure in the common chamber 112, the mercury chamber 174, the annular space 130, the sample volume 126, the transducer sub-assembly 108, and the vacuum fluid line 182 to absolute 0 psi or about 0 psi as measured by the transducers 114, 160, 162, 226.

The vacuum valve 190, the first connection valve 206, the second connection valve 208, and the annular valve 212 are closed, isolating the mercury chamber 174, the vacuum pump 180, the annular space 130, and the sample volume 126, from the common chamber and from each other.

The mercury valve 178 is opened and the mercury pump fills the mercury chamber 174 so that a known amount of mercury is in the mercury chamber 174. The mercury is pumped until the mercury level reaches a marker 174a. The volume of the mercury chamber 174 is equal to or greater than the volume of the sample volume 126 with the volume of the tubing 134. The first connection valve 206 is opened to fluidly connect the mercury chamber 174 with the tubing 134 and sample volume 126. Mercury flows through the mercury tubing 170, the connection tubing 204, and tubing 134 to fill the sample volume 126 and tubing 134. The change in mercury, observable in the mercury chamber 174, corresponds to the mercury level in the sample volume 126. The mercury continues to fill the tubing 134 and sample volume 126 until the mercury passes a marked volume, level, or sensor.

The first connection valve 206 is closed to disconnect the common chamber 112 from the mercury chamber 174. The second hydraulic fluid valve 159 and the second indicator fluid valve 193 are opened so that the annular space 130, the fluid source 149, and the fluid indicator 186 are in fluid connection with each other. Fluid flows, by gravity or by a pump, from the fluid source 149 into the annular space 130 of the casing 116. When fluid from the fluid source 149 enters the fluid indicator 188, the annular space 130 is filled with the hydraulic fluid. The indicator fluid line 188 may include a check valve to prevent indicator fluid from returning to the annular space 130 of the casing 116. The second hydraulic valve 159 and the second indicator fluid valve 193 are closed and the annular space 130, filled with hydraulic fluid, is isolated from the fluid indicator 186 and the fluid source 149. At this stage, the apparatus is set up and primed to begin low pressure measurements to generate a capillary pressure curve of the rock sample 128 in the penetrometer 122.

To begin the low-pressure measurement phase of a single-stage measurement, the low-pressure valve 154 is opened, fluidly connecting the gas cylinder 152 to the common chamber 112 via the low-pressure inlet 218. Gas from the cylinder moves, or is pumped, into the interior volume 202 of the common chamber, and the third connection valve 209 (a check valve) is opened. The apparatus applies a low pressure (e.g., 0 psi to 30 psi) to the sample volume 126 of the penetrometer 122. The gas from the cylinder enters the third connection valve 209, and will apply pressure to the mercury in the tubing 134, transferring the pressure via a gas-mercury interface (not shown) to the rock sample 128 in the sample volume 126. The pressure is recorded by the low pressure transducers 160 in the transducer sub-assembly 108. The mercury level in the tubing 134 (or the gas-mercury interface) is also recording and transmitted to the computer system 194. In some systems, the mercury level is determined by measuring the capacitance of the tubing using the electric plug.

The gas continues to enter the tubing 134 via the third connection valve 209, increasing from a pressure of 0 psi to 40 psi. Some of the threshold valves 166 of the pressure transducer sub-assembly 108 may trigger to isolate sensitive low pressure transducers 160 as the pressure increases.

Once 40 psi, or another predetermined pressure, is reached, the apparatus enters the high-pressure phase of the single stage method 250. The sample 128 and penetrometer 122 remain in the casing 116 and the low pressure valve 154 and third connection valve 209 are closed, thereby isolating the common chamber 112 from the low pressure fluid circuit 106. The common chamber 112 is then fluidically connected to the high pressure fluid circuit by opening the high pressure valve 145. The first hydraulic fluid valve 158 and the first indicator fluid valve 192 are opened to fluidly connect the fluid source 149 with the interior volume 202 of the common chamber and the fluid indicator 186. Hydraulic fluid from the fluid source 149 is moved, by gravity or by a pump, into the interior volume 202 of the common chamber 112. The gas in the common chamber 112 can be vented out of the common chamber 112 via an exhaust line 166e. When fluid from the fluid source 149 enters the fluid indicator 186, the interior volume 202 of the common chamber 112 is filled with the hydraulic fluid. The first hydraulic fluid valve 158 and the first indicator fluid valve 192 are closed to fluidly isolate the fluid source 149, the fluid indicator 186, and the interior volume 202 of the common chamber 112 from each other. The threshold valves 166a, 166b 166c, 166d, 166e may be closed to prevent damage to the low pressure transducers 160. At this stage, the apparatus is set up and primed to begin high pressure measurements to generate a capillary pressure curve of the rock sample 128 in the penetrometer 122.

The annular valve 212 is opened to fluidly connect the interior volume 202 of the common chamber 112 with the annular space 130 of the casing 116. The pressures measured at the first transducer 114 and the second transducers 226 are equal. The high pressure fluid circuit flows fluid into the common chamber 112 to increase the pressure in the annular space 130 from 30 psi to 60,000 psi, over a period of time. The high pressure fluid pressurizes the penetrometer through the second connection valve 208. In this configuration the pressure in the annular space 130 is equal to the pressure in the sample volume 126 of the penetrometer 122 and the interior volume 202 of the common chamber 112. The pressure gradually increases simultaneously in the common chamber 112, penetrometer 122, and annular space 130 to about 60,000 psi, or another predetermined maximum test pressure. The high pressure transducers 162 measure the pressure and transmit the pressure to the computer system 194. Some of the threshold valves 166 of the pressure transducer sub-assembly 108 may trigger to isolate sensitive pressure transducers 160, 162 as the pressure increases. The mercury level in the tubing 134 (or the gas-mercury interface) is also recording and transmitted to the computer system 194, as the pressure increases.

Figure 4:
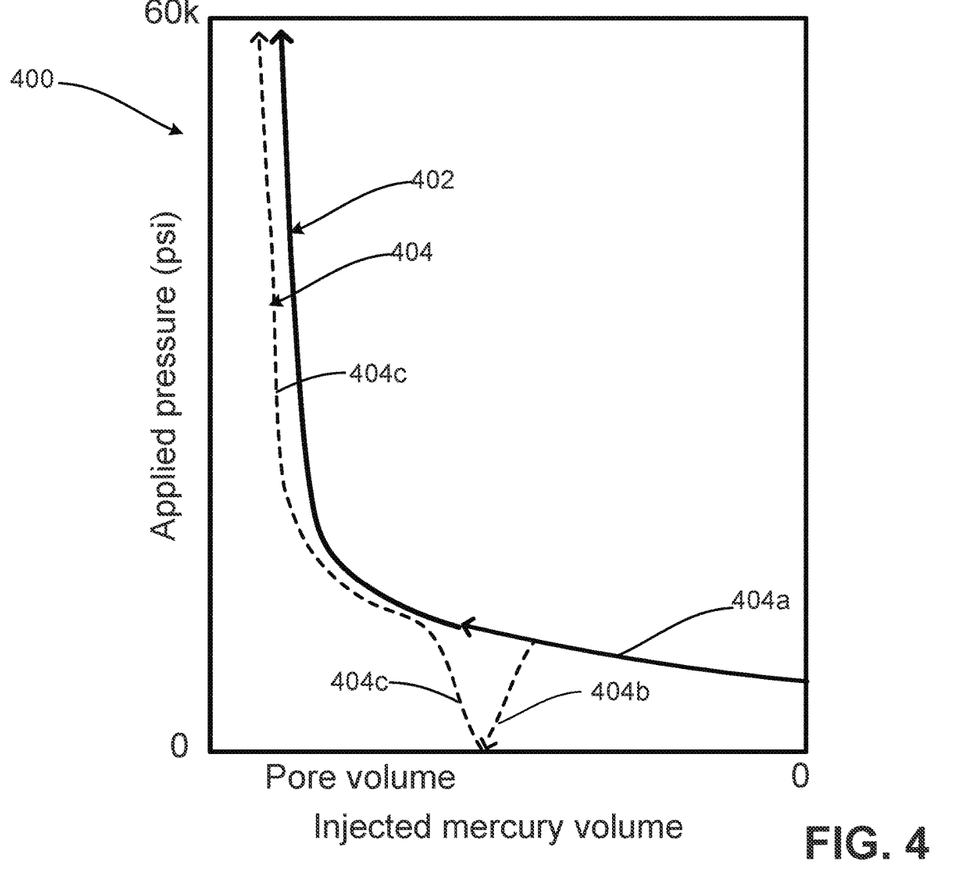
FIG. 4 is a pressure graphs of a single stage MICP measurement apparatus compared to a two-stage MICP measurement apparatus.

When the pressure has reached 60,000 psi or a different predetermined pressure, the single-stage test is complete. The high pressure fluid circuit 104 is disconnected from the common chamber 121 by closing the high pressure valve 145 and the fluid in the casing 116, tubing 134, and common chamber 112 is discharged through exhaust fluid lines. The casing 116 is opened to remove the penetrometer 122. The computer system 194 generates a capillary pressure curve, for example as shown in FIG. 4, based on the measured mercury levels and measured pressures. For example, the computer system may plot all transducer pressure data vs. measured mercury levels (volume) in a single graph. This graph results in a 0 psi to 60,000 psi continuous MICP curve without interruptions in the middle of the test.

FIG. 4 is pressure graph 400 of a single stage MICP measurement apparatus as compared to a two stage MICP measurement apparatus. The pore volume is measured by the penetrometer as the pressure increased from 0 psi to 60,000 psi. The first trend line 402 is a capillary pressure curve generated by a single stage MICP measurement apparatus, for example the apparatus 100. The second (dotted) trend line 404 is capillary pressure curve generated by a two stage MICP measurement apparatus. The second trend line 404 has four portions, a low pressure portion 404a, a depressurizing portion 404b, a repressurizing portion 404c, and a high pressure portion 404d. The valley between the depressurizing portion 404b and a repressurizing portion 404c occurs when the sample is removed from a low pressure testing site and moved to a different, high pressure testing site, disrupting data collection and producing inconsistency within the collected measurements. The first trend line 402 generated by the date of the stage MICP measurement apparatus does not include a valley. The capillary pressure curve generated by the single stage MICP measurement apparatus is a continuous, smooth curve, because the pore volume is measured continuously in a single sample chamber as the pressure increases from 0 psi to 60,000 psi. The single stage MICP measurement apparatus can reduce the risk of inconsistent data by reducing the need for data extrapolation and estimation In some methods, pressure measurements are taken sequentially by the transducers. For example, the controller may prompt the first low pressure transducer to measure a pressure, then, after the pressure has met or exceeded the maximum measurable pressure of the first low pressure transducer, the controller prompts the second low pressure transducer to measure the pressure. The second low pressure transducer continues to measure the pressure until the pressure meets or exceeds the maximum measurable pressure of the second low pressure transducer. The controller prompts the third low pressure transducer to measure the pressure. The system applies these steps to each of the low pressure transducers and high pressure transducers. In some cases the controller may prompt the corresponding threshold valve to close when the maximum measurable pressure of a transducer has been reached.

In some cases, to smoothly transition between transducer measurements, the subsequent transducer measurement may start before the previous transducer measurement ends for example, the controller may prompt the second low pressure transducer to measure the pressure at 0.5 psi while the first low pressure transducer has a maximum measurable pressure of 0.7 psi. The controller receives measurement data with pressure measurements from both the (first low) pressure transducer and the subsequent (second low) pressure transducer. Overlapped measurement data generated by both the first low pressure transducer and the second low pressure transducer between 0.5 and 0.7 psi may improve measurement quality, consistency, and accuracy.

While a transducer sub-assembly having high pressure transducers and low-pressure transducers has been described, some transducer sub-assembly include a plurality of transducers. Some of the transducers are configured to measure pressure ranges that overlap for continuous pressure measurements, for example a first transducer with a measurement range of 0 psi to 0.7 psi and a second transducer with a measurement range of 0.5 psi to 1.5 psi While an pressure transducer sub-assembly has been described with eight pressure transducers, some pressure transducer sub-assemblies have more than eight pressure transducers or less than eight pressure transducers, for example one, two, three, four, five, six, seven, nine, ten, eleven, twelve, thirteen, fourteen, fifteen, twenty, thirty, fourth, fifty, sixty, seventy, eighty, ninety, one hundred, or two hundred pressure transducers.

A number of embodiments have been described. Nevertheless, it will be understood that various modifications may be made without departing from the spirit and scope. Accordingly, other embodiments are within the scope of the following claims.

What is claimed is:

1. A mercury injection capillary pressure (MICP) measurement apparatus comprising:
   a sample sub-assembly comprising:
      a casing having walls defining an interior volume,
      a penetrometer arranged in the casing, the penetrometer having walls defining a sample volume,
      an annular space defined between the walls of the casing and the walls of the penetrometer, and
      a common chamber fluidly connected to the annular space by a fluid line and to the sample volume of the penetrometer by a tubing,
   a transducer sub-assembly fluidly connected to the sample sub-assembly via the common chamber, the transducer sub assembly comprising:
      a plurality of high-pressure transducers configured to measure a pressure above 30 psi, and
      a plurality of low-pressure transducers configured to measure a pressure below 40 psi;
   a hydraulic intensifier fluidly connected to the common chamber and configured to apply a high pressure to the annular space, and
   a gas tank in fluid connection with the common chamber and configured to apply a low pressure to the sample volume of the penetrometer.

2. The MICP measurement apparatus of claim 1, wherein the apparatus comprises a mercury source and mercury chamber, wherein the mercury chamber is fluidly connected to the common chamber.

3. The MICP measurement apparatus of claim 2, wherein the mercury source is fluidly connected to the sample volume of the penetrometer.

4. The MICP measurement apparatus of claim 1, wherein the plurality of high pressure transducers comprises:
   a transducer configured to measure a pressure between 30 psi and 130 psi.

5. The MICP measurement apparatus of claim 1, wherein the plurality of high pressure transducers comprises:
   a transducer configured to measure a pressure between 100 psi and 600 psi.

6. The MICP measurement apparatus of claim 1, wherein the plurality of high pressure transducers comprises:
   a transducer configured to measure a pressure between 500 psi and 6,000 psi.

7. The MICP measurement apparatus of claim 1 wherein the plurality of high pressure transducers comprises:
   a transducer configured to measure a pressure between 5,000 psi and 60,000 psi.

8. The MICP measurement apparatus of claim 1, wherein the plurality of low-pressure transducers comprises:
a transducer configured to measure a pressure between 0 psi and 0.7 psi.

9. The MICP measurement apparatus of claim 1, wherein the plurality of low pressure transducers comprises:
a transducer configured to measure a pressure between 0.5 psi and 1.5 psi.

10. The MICP measurement apparatus of claim 1, wherein the plurality of low pressure transducers comprises:
a transducer configured to measure a pressure between 1 psi and 7 psi.

11. The MICP measurement apparatus of claim 1, wherein the plurality of low pressure transducers comprises:
a transducer configured to measure a pressure between 5 psi and 15 psi.

12. The MICP measurement apparatus of claim 1, wherein the plurality of low pressure transducers comprises:
a transducer configured to measure a pressure between 10 psi and 40 psi.

13. The MICP measurement apparatus of claim 1, wherein each of the low pressure transducers in the plurality of low pressure transducers are connected to the chamber via a low pressure fluid line of a plurality of low pressure fluid lines.

14. The MICP measurement apparatus of claim 13, wherein a low pressure threshold valve is arranged on each of the low pressure fluid lines and is configured to close at a threshold pressure.

15. The MICP measurement apparatus of claim 1, wherein each of the high pressure transducers in the plurality of high pressure transducers are connected to the chamber via a high pressure fluid line of a plurality of high pressure fluid lines.

16. The MICP measurement apparatus of claim 15, wherein a high pressure threshold valve is arranged on each of the high pressure fluid lines and is configured to close at a threshold pressure.

17. The MICP measurement apparatus of claim 1, wherein the sample volume is configured to contain a porous medium sample, wherein the porous medium sample is a consolidated rock sample, an unconsolidated rock sample, a soil sample, a powder sample, or a combination thereof.

18. The MICP measurement apparatus of claim 1, further comprising a first pressure transducer arranged in the common chamber and a second pressure transducer arranged in the annular space of the casing.

19. The MICP measurement apparatus of claim 1, further comprising a valve arranged on the fluid line.

20. The MICP measurement apparatus of claim 1, further comprising a vacuum pump fluidly connected to the common chamber.

21. A method to test a rock sample in a single stage MICP apparatus, the method comprising:
applying, in a stage, a low pressure to a sample volume of a penetrometer in a single stage MICP apparatus; and
applying, in the same stage, a high pressure to the sample volume of the penetrometer in the single stage MICP apparatus, wherein applying, in the stage, the low pressure to the sample volume of a penetrometer in the single stage MICP apparatus comprises:
controlling a pressure by flowing a gas from a gas cylinder to the sample volume.

22. The method of claim 21, wherein applying, in the stage, the low pressure to the sample volume of a penetrometer in the single stage MICP apparatus comprises:
increasing the pressure from 0 psi to 40 psi over a predetermine period of time.

23. The method of claim 21, wherein applying, in the stage, the low pressure to the sample volume of a penetrometer in the single stage MICP apparatus comprises:
measuring a mercury level in the apparatus.

24. The method of claim 23, wherein applying, in the same stage, the high pressure to the sample volume of a penetrometer in the single stage MICP apparatus comprises:
measuring a mercury level in the apparatus.

25. The method of claim 24, further comprising:
generating, by a controller of the apparatus, a continuous MICP curve.

26. The method of claim 21, wherein applying, in the same stage, the high pressure to the sample volume of a penetrometer in the single stage MICP apparatus comprises:
controlling a pressure by flowing a gas from a hydraulic intensifier.

27. The method of claim 21, wherein applying, in the same stage, the high pressure to the sample volume of a penetrometer in the single stage MICP apparatus comprises:
increasing the pressure from 30 psi to 60,000 psi over a predetermine period of time.

* * * * *